(12) United States Patent
Willard

(10) Patent No.: US 12,274,648 B2
(45) Date of Patent: Apr. 15, 2025

(54) ANTERIOR BOOT FOR HIP DISTRACTION

(71) Applicant: Conmed Corporation, Largo, FL (US)

(72) Inventor: Benjamin Willard, Clearwater, FL (US)

(73) Assignee: Conmed Corporation, Largo, FL (US)

( * ) Notice: Subject to any disclaimer, the term of this patent is extended or adjusted under 35 U.S.C. 154(b) by 0 days.

(21) Appl. No.: 18/478,055

(22) Filed: Sep. 29, 2023

(65) Prior Publication Data

US 2024/0024185 A1 Jan. 25, 2024

Related U.S. Application Data

(62) Division of application No. 16/407,356, filed on May 9, 2019, now Pat. No. 11,806,286.

(60) Provisional application No. 62/668,834, filed on May 9, 2018, provisional application No. 62/668,854, filed on May 9, 2018, provisional application No. 62/668,893, filed on May 9, 2018.

(51) Int. Cl.
*A61G 12/00* (2006.01)
*A61F 5/37* (2006.01)
*A61G 13/12* (2006.01)

(52) U.S. Cl.
CPC ........ *A61G 13/1295* (2013.01); *A61F 5/3761* (2013.01); *A61G 13/125* (2013.01); *A61G 13/1275* (2013.01); *A61G 13/129* (2013.01)

(58) Field of Classification Search
CPC .............. A61G 13/125; A61G 13/1275; A61G 13/129; A61G 13/124; A61G 13/1295; A61G 13/12; A61G 13/1245; A61G 7/065; A61G 7/075; A61G 7/0755; A61G 7/1082; A61G 7/1096; A61G 7/109; A61G 2200/32; A61F 5/3761; A61F 5/3769; A61H 1/022; A61H 1/0266; A63B 23/08; A63B 23/10
USPC ...................................................... 128/845
See application file for complete search history.

(56) References Cited

U.S. PATENT DOCUMENTS

| | | | | |
|---|---|---|---|---|
| 1,239,789 | A * | 9/1917 | Hawley ................ | A61H 1/0218 602/36 |
| 2,783,758 | A * | 3/1957 | Trott ......................... | A61F 5/04 602/33 |
| 3,872,861 | A * | 3/1975 | Tamny ...................... | A61F 5/04 602/36 |
| 2010/0018537 | A1 * | 1/2010 | Soto ........................ | A61G 13/12 128/845 |
| 2010/0069809 | A1 * | 3/2010 | Sommers .................. | A61F 5/04 602/32 |

(Continued)

*Primary Examiner* — Adam Baker
(74) *Attorney, Agent, or Firm* — Bond, Schoeneck & King, PLLC; Frederick J. M. Price

(57) ABSTRACT

A surgical boot system and sleeve accessory for hip distraction. The surgical boot system includes an L-shaped rigid shell having a proximal portion and a distal portion. A soft liner is attached to the rigid shell and extends along at least one of the proximal portion and the distal portion. The surgical boot system also includes at least one strap assembly (which can be a plurality of strap assemblies) extending around the rigid shell. A load transmission hoop is connected to and extends around the distal portion of the rigid shell and an attachment point is connected to the load transmission hoop. The rigid shell is pivotable about the attachment point. Specifically, the attachment point is configured to interface with a hip distractor apparatus in a way that allows for multiple degrees of freedom.

8 Claims, 8 Drawing Sheets

(56) References Cited

U.S. PATENT DOCUMENTS

2011/0185506 A1* 8/2011 Broens ............... A61G 13/12
5/648
2013/0305454 A1* 11/2013 Ben-Galim ........... A61F 5/3776
5/628

* cited by examiner

ANTERIOR BOOT FOR HIP DISTRACTION

CROSS-REFERENCE TO RELATED APPLICATIONS

This application is a division of U.S. Non-Provisional patent application Ser. No. 16/073,056, filed on May 9, 2019, which claims priority to U.S. Provisional Patent Application Ser. No. 62/668,834, filed on May 9, 2018 and entitled "Anterior Boot for Hip Distraction," U.S. Provisional Patent Application Ser. No. 62/668,854, filed on May 9, 2018 and entitled "Vacuum Fixated Sleeve for Hip Distraction," and U.S. Provisional Patent Application Ser. No. 62/668,893, filed on May 9, 2018 and entitled "Finger Trap Sleeve for Hip Distraction," the entireties of which are incorporated herein by reference.

BACKGROUND OF THE INVENTION

1. Field of the Invention

The present disclosure is directed generally to a surgical system and, more particularly, to a surgical boot system and sleeve accessory for hip distraction.

2. Description of Related Art

Current distraction of the hip joint, such as during arthroscopic hip surgical procedures, is reliant upon the application of pulling forces on the foot and leg of the operative side. The means of interfacing with the foot and leg to achieve the holding necessary to apply these forces is currently accomplished with a boot fastened to the foot and leg, resembling a ski boot. This boot often typically consists of a rigid shell that interfaces with the posterior of the leg and the plantar surface of the foot, and the leg and foot is held down into this shell with straps, pads under straps, and occasionally a rigid or non-rigid anterior shell. These boots are known to sometimes allow the leg and foot to slip, allowing the leg to migrate proximally which has the effect during arthroscopic hip procedures of causing the opening made in the hip joint to collapse closed to its former non-distracted position.

Therefore, there is a need for a better system and apparatus for securing the leg during hip distraction procedures.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

SUMMARY OF THE INVENTION

Embodiments of the present invention are directed to a surgical boot system and sleeve accessory for hip distraction. According to one aspect, the present invention is a surgical boot system. The surgical boot system includes an L-shaped rigid shell having a proximal portion and a distal portion. A soft liner is attached to the rigid shell and extends along the proximal portion and the distal portion. The surgical boot system also includes a plurality of strap assemblies extending around the rigid shell. A load transmission hoop is connected to and extends around the distal portion of the rigid shell and an attachment point is connected to the load transmission hoop. The rigid shell is pivotable about the attachment point.

According to another aspect, the present invention is a surgical sleeve accessory. The sleeve accessory includes a tubular body having a proximal end and a distal end with an inner volume extending therebetween. The inner volume has a central longitudinal axis extending therethrough. The tubular body is comprised of one or more strands of material woven into a braided construction. A helix angle is measured between the central longitudinal axis and one of the one or more strands of material. The helix angle can be within the range of 20° to 70°. The surgical sleeve accessory additionally includes a collection point distal relative to the distal end of the tubular body wherein a distal end of each of the one or more strands of material is gathered.

According to yet another aspect, the present invention is a vacuum surgical sleeve accessory. The vacuum surgical sleeve accessory includes a tubular body having a proximal end and a distal end with an inner volume extending therebetween. An internal material is within the tubular body and extends between the proximal end and the distal end. The vacuum surgical sleeve accessory also includes a vacuum port connected to the internal material and extending from the tubular body. Additionally, there are one or more external straps attached to and extending along an exterior surface of the tubular body past the distal end.

These and other aspects of the invention will be apparent from and elucidated with reference to the embodiment(s) described hereinafter.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
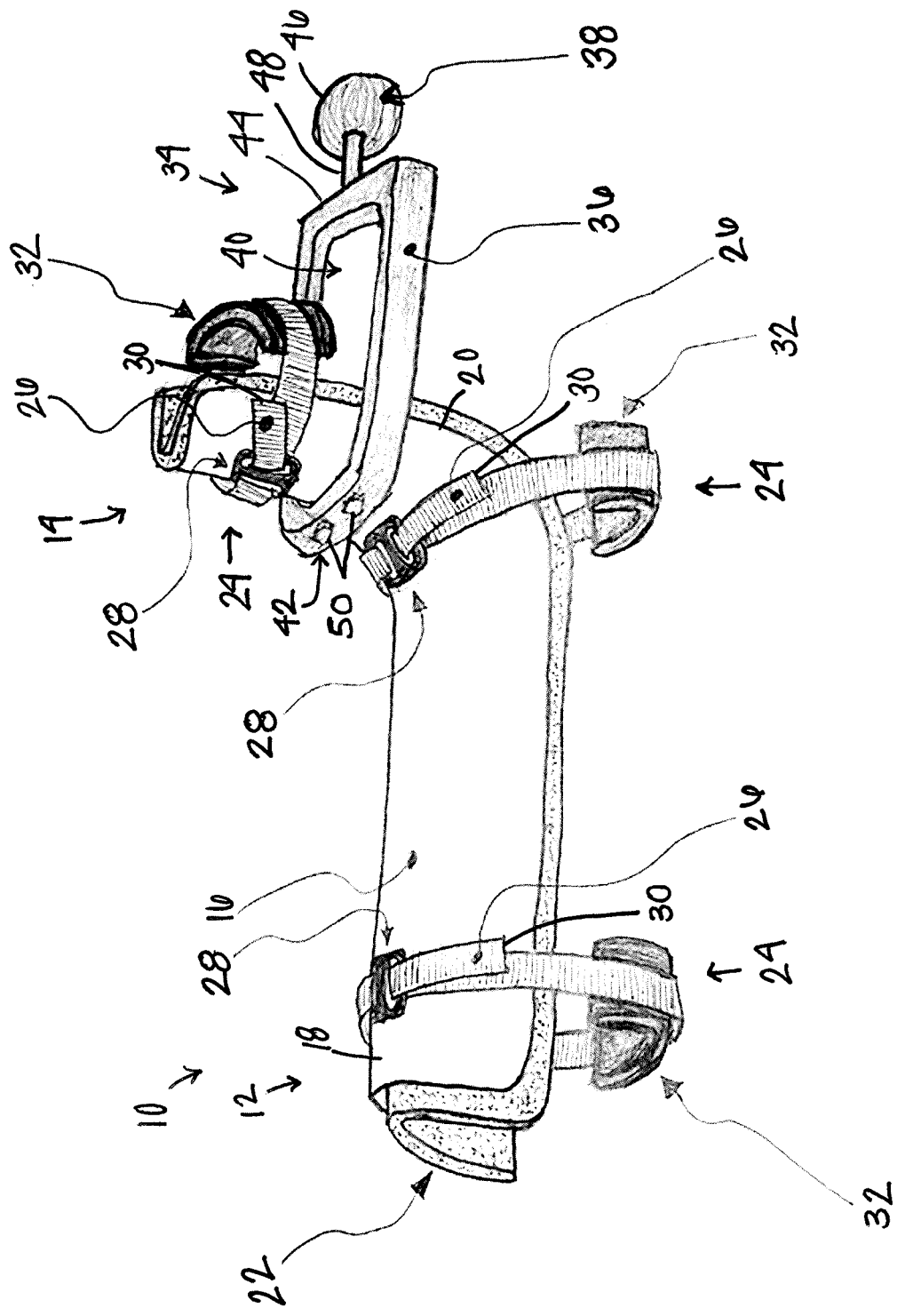
FIG. 1 is a side view schematic representation of a surgical boot, according to an embodiment.
Figure 3:
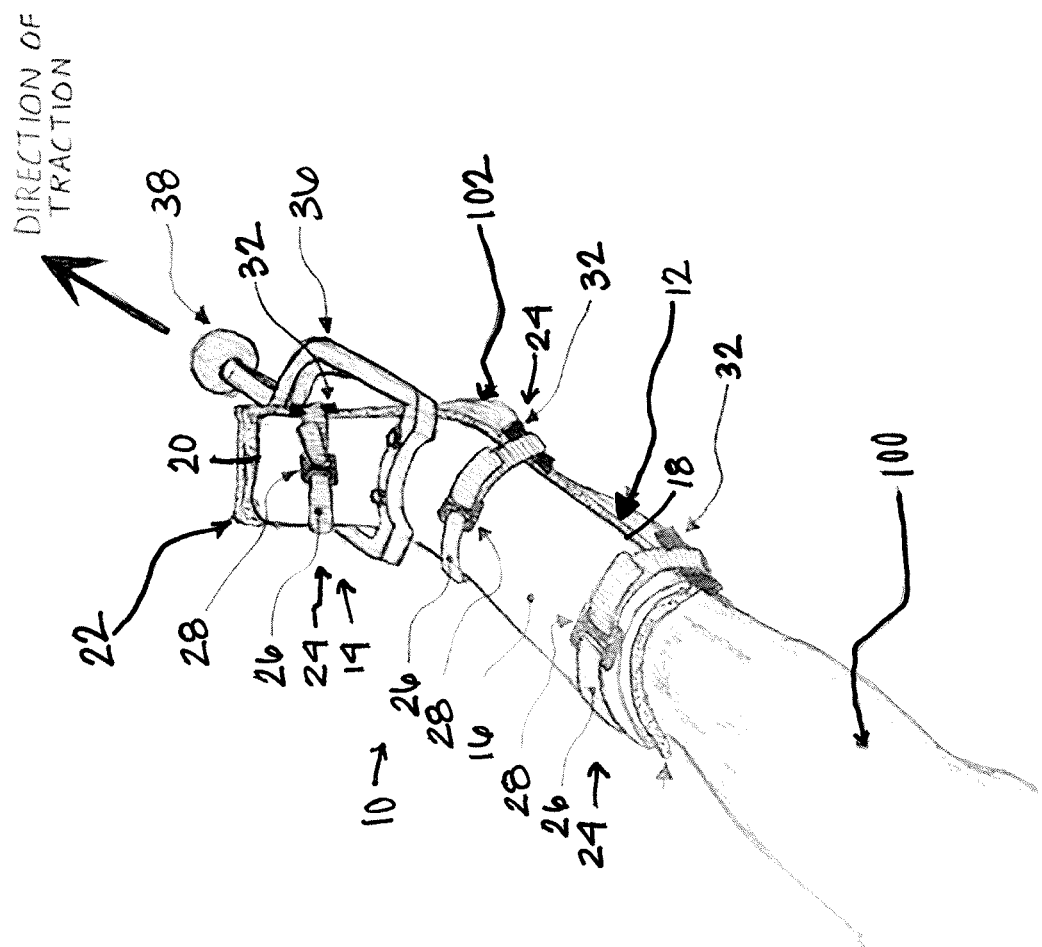
FIG. 3 is a proximal perspective view schematic representation of the surgical boot in use, according to an embodiment.
Figure 4:
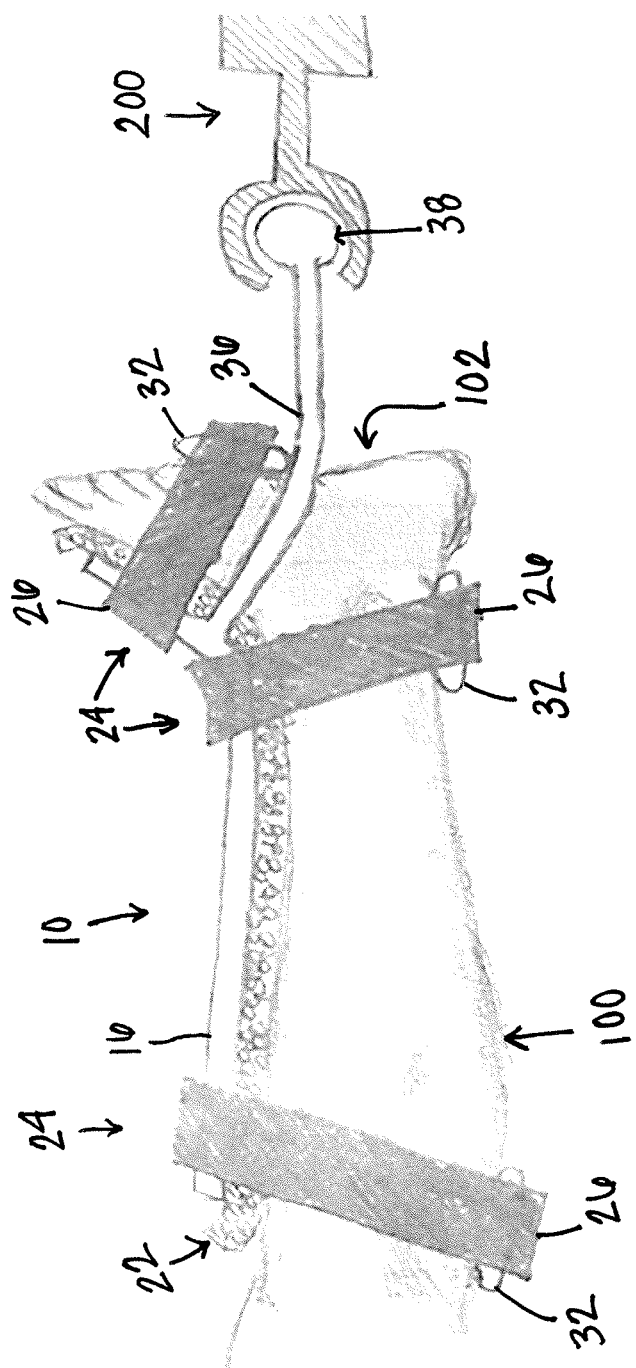
FIG. 4 is a side view schematic representation of the surgical boot in use, according to an embodiment.

Referring now to the figures, wherein like reference numerals refer to like parts throughout, FIG. 1 shows a side view schematic representation of a surgical boot 10, according to an embodiment. The surgical boot 10 has a proximal end 12 and a distal end 14. The surgical boot 10 includes a rigid shell 16. The rigid shell 16 is generally L-shaped, having a proximal portion 18 and a distal portion 20. The proximal portion 18 is complimentary to the anterior of the leg 100 (FIGS. 3-4) and the distal portion 20 is complimentary to the dorsal surface of the foot 102 (FIGS. 3-4). The rigid shell 16 can be scaled to accommodate smaller users (e.g., pediatric patients) or larger users (e.g., tall adult patients). The rigid shell 16 can be composed of any rigid material, such as plastic or composite material.

Still referring to FIG. 1, the surgical boot 10 additionally can include a soft liner 22. As shown in FIG. 1, the soft liner 22 is generally L-shaped, like the rigid shell 16, with portions complimentary to the anterior of the leg 100 (FIGS. 3-4) and the dorsal surface of the foot 102 (FIGS. 3-4). The soft liner 22 is configured for positioning between the leg and foot of the user and the rigid shell 16. The soft liner 22 protects the tissue of the user from excessive contact pressure against the rigid shell 16. The soft liner 22 can be composed of any compressible material, such as open-cell foam, closed-cell foam, and gel pad material, for example.

In an embodiment, the soft liner 22 is attached to the rigid shell 16. The soft liner 22 can be fixed to the rigid shell 16 with an adhesive. Alternatively, the soft liner 22 can be removably attached to the rigid shell 16. For example, the soft liner 22 may comprise hook and loop fasteners which mate with or otherwise attach to hook and loop fasteners on the rigid shell 16. In another example, the soft liner 22 may comprise a temporary adhesive for removable attachment to the rigid shell 16. Any other known connectors or means for temporary attachment can be used, as should be understood by a person of ordinary skill in the art in conjunction with a review of this disclosure.

Still referring to FIG. 1, the surgical boot 10 can include one or more strap assemblies 24 that secure the rigid shell 16 and soft liner 22 to the leg and foot of the user. Any number of strap assemblies 24 can be used. In the depicted embodiment, three strap assemblies 24 are used. The strap assemblies 24 each include a strap 26. The strap 26 is used to gain purchase on a region of the user's leg or foot. The strap 26 can be composed of flexible material such that the strap 26 can be used to tightly secure the user's leg and/or foot to the soft liner 22 and the rigid shell 16.

The strap assemblies 24 each may also include adjustment mechanism 28. In the depicted embodiment, the adjustment mechanism 28 is a buckle. The strap 26 may also comprise connectors, such as hook and loop fasteners, on an end 30 of the strap 26 such that when the strap 26 has been appropriately tensioned via the adjustment mechanism 28, the end 30 of the strap 26 can be secured to another portion of the strap 26.

While the adjustment mechanism 28 allows for tightening and loosening the strap 26, the adjustment mechanism 28 also prevents the strap 26 from sliding along the rigid shell 16. In the depicted embodiment, the buckle 28 is attached to the rigid shell 16 to prevent proximal or distal migration of the strap 26 under distraction forces. However, other means may be used to prevent migration of the strap 26, such as ratcheting buckles, D-ring loops, and the like. Similarly, apertures resembling those of the buckle 28 can be machined into the rigid shell 16 for the strap 26 so that the adjustment mechanism 28 is built into the rigid shell 16.

The strap assemblies 24 can additionally include a strap pad 32. The strap pad 32 can be a piece of material that prevents excessive localized pressure when the strap 26 is tightened around the leg and foot. The strap pad 32 is comprised of foam, gel, or any other soft, compressible material. In the depicted embodiment, the strap pad 32 is rectangular in order to widely disperse pressure. However, the strap pad 32 can be sized, shaped, and otherwise configured to maximize the dispersion of pressure for a particular sized patient. In FIG. 1, the strap 26 is fixed to the strap pad 32, but the strap 26 may be removably attached to the strap pad 32, woven therethrough or attached via connectors, for example.

In the embodiment shown in FIG. 1, there are three strap assemblies 24. A first strap assembly 24 is used at a proximal end 12 of the surgical boot 10. The first strap assembly 24 is intended to gain purchase on a proximal region of the prominence of the user's calf. A second strap assembly 24 is used in an intermediate position between the proximal end 12 and the distal end 14 of the surgical boot 10. In the depicted embodiment, the second strap assembly 24 is used to gain purchase on the proximal region of the prominence of the posterior of the ankle. A third strap assembly 24 is used at the distal end 14 of the surgical boot 10. The third strap assembly 24 is used to secure the metatarsal region of the foot to the dorsal region of the rigid shell 16 and prevent the foot from going into plantarflexion. This prevents the foot from escaping the surgical boot 10 while still allowing the leg to migrate out of the surgical boot 10 in a direction opposite of the traction.

Still referring to FIG. 1, traction in the distal direction is applied to the surgical boot 10 by a tractioning mechanism 34. The tractioning mechanism 34 includes a load transmission hoop 36 with an attachment point 38. The load transmission hoop 36 can be a ring, loop, or other enclosed piece of material with an aperture 40 extending therethrough. In the depicted embodiment, the load transmission hoop 36 is D-shaped, having a rounded end 42 and a straight end 44 with the attachment point 38 connected to the straight end 44. In other embodiments, the load transmission hoop 36 can be rectangular, circular, or any other suitable geometry. The load transmission hoop 36 can be composed of any suitable rigid material, such as metal, plastic, or composite. The load transmission hoop 36 transmits load from the rigid shell 16 as it applies traction to the leg and foot. The load is transmitted around the foot and delivers it to the attachment point 38.

As mentioned above, the load transmission hoop 36 comprises an attachment point 38 connected to the straight end 44 of the load transmission hoop 36. The attachment point 38 is configured to interface with a hip distractor apparatus (not shown). In the depicted embodiment, the attachment point 38 is a sphere 46 connected to the load transmission hoop 36 via a shaft 48. However, the attachment point 38 can have any number of forms, depending on the interface of the particular distractor apparatus. The sphere 46 shown in FIG. 1 is one possible interface with a distractor apparatus where the distractor apparatus is configured to receive the sphere 46 to allow the surgical boot 10 to pivot, rock, and rotate. The attachment point 38 is composed of material that interfaces with the distractor apparatus in a manner intended for that particular distractor apparatus, which can be metal, although plastic or composite can also be used.

Figure 2:
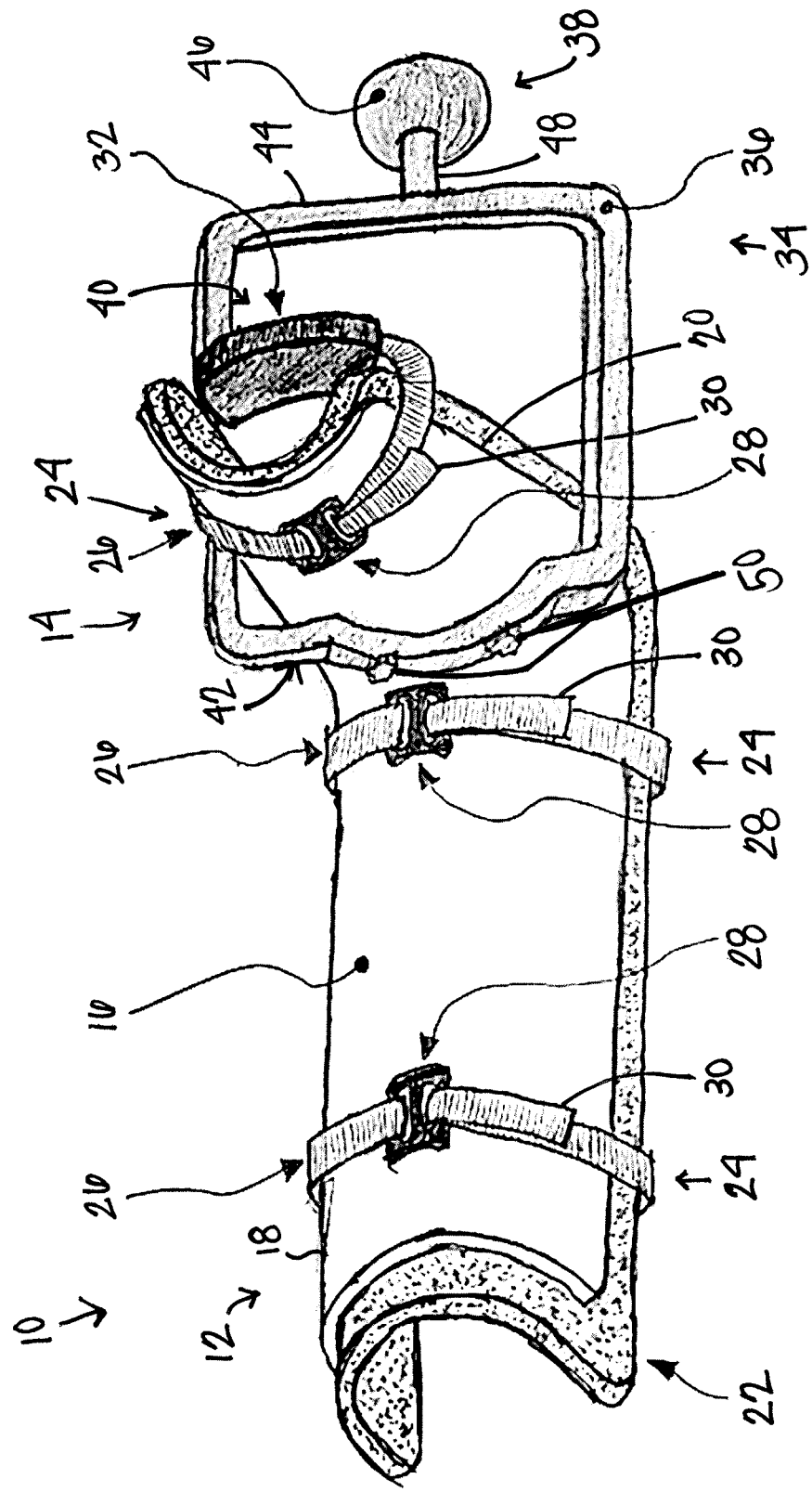
FIG. 2 is a top perspective view schematic representation of the surgical boot, according to an embodiment.

Turning now to FIG. 2, there is shown a top perspective view schematic representation of the surgical boot 10, according to an embodiment. As shown in FIG. 2, the load transmission hoop 36 is removably attached to the rigid shell 16 via one or more connectors 50. In the depicted embodiment, the connectors 50 are screws; however, any known connectors 50 may be used. The connectors 50 maintain the positioning of the load transmission hoop 36 along the rigid shell 16, which can be critical for the proper application of traction in certain embodiments.

Referring now to FIGS. 3 and 4, there is shown a proximal perspective view schematic representation and a side view schematic representation, respectively, of the surgical boot 10 in use, according to an embodiment. As shown in FIGS. 3-4, a patient's foot 102 and leg 100 have been inserted into the surgical boot 10. The leg 100 and foot 102 of the patient are positioned within the surgical boot 10 such that the leg (i.e., calf) 100 and the foot 102 of the patient are against the soft liner 22, as shown in FIG. 4. In other words, the soft liner 22 of the surgical boot is between the rigid shell 16 and the leg 100 and foot 102 of the patient. The three strap assemblies 24 are shown tightened around the rigid shell 16 and the leg 100 and foot 102 of the patient.

With the patient's leg 100 and foot 102 secured within the surgical boot 10, the attachment point 38 (connected to the load transmission hoop 36) is connected to a distractor apparatus 200, as shown in FIG. 4. The attachment point 38 is connected to the distractor apparatus 200 in a way that allows for multiple degrees of freedom. In other words, the surgical boot 10 may pivot in a number of degrees of freedom. As pulling forces are applied to the attachment point 38 by the distractor apparatus 200, the foot 102 and leg 100 are positively held.

Figure 5:
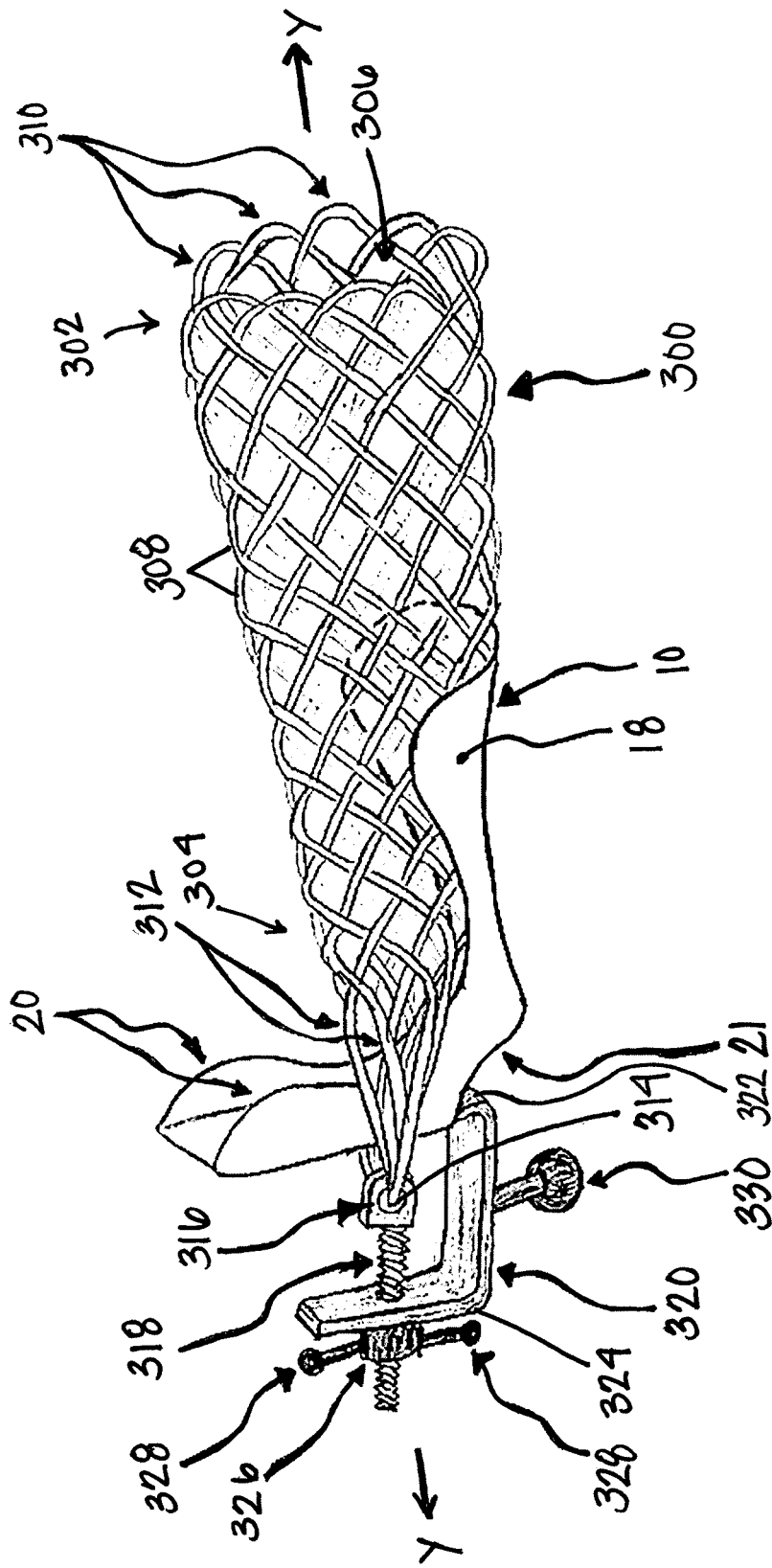
FIG. 5 is a side view schematic representation of a sleeve accessory, according to an embodiment.
Figure 6:
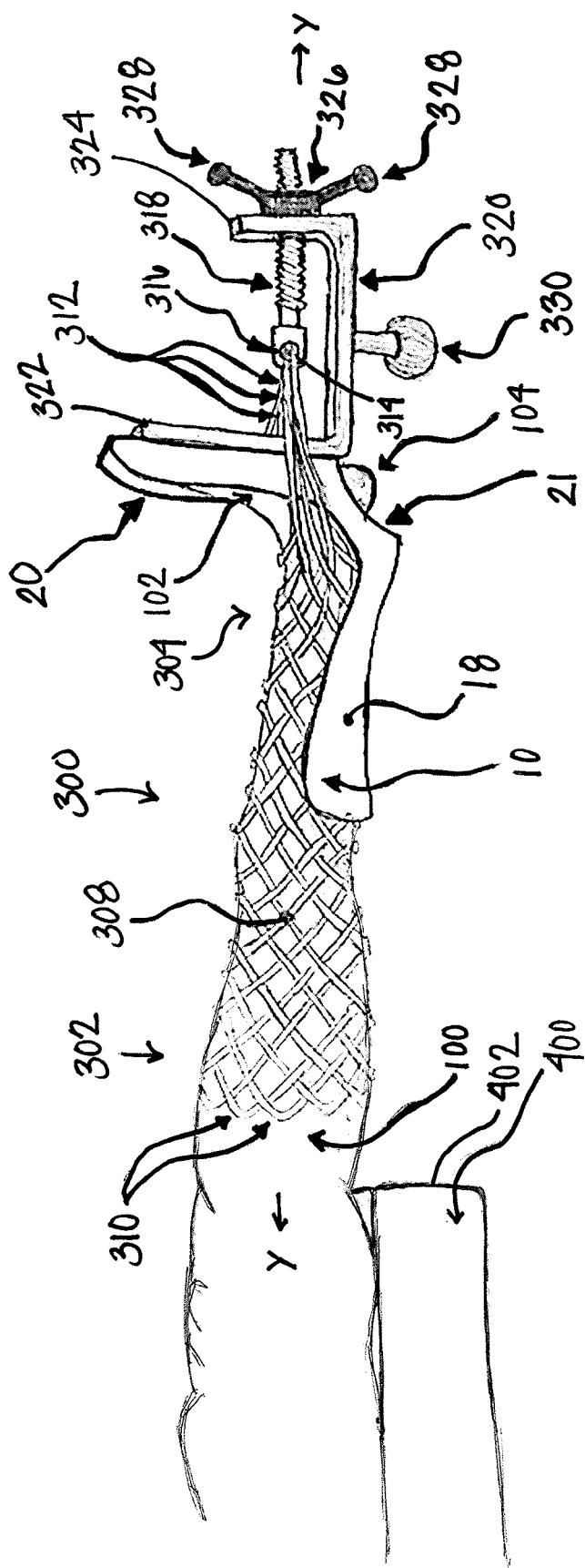
FIG. 6 is a side view schematic representation of a sleeve accessory in use, according to an embodiment.

Turning now to FIGS. 5 and 6, there are shown side views schematic representations of a sleeve accessory 300, according to an embodiment. The sleeve accessory 300 shown in FIGS. 6 and 6 is a "finger trap" sleeve configured to fit around a patient's leg. As shown in FIG. 5, the sleeve accessory 300 is a tubular body, having a proximal end 302 and a distal end 304 with an inner volume 306 for the patient's leg extending therebetween. In the depicted embodiment, the sleeve accessory 300 is composed of one or more strands of material 308 braided or otherwise woven into the tubular shape.

The strands of material 308 can be composed of braided fibrous material, narrow film material, or any other suitable flexible material. Strips of solid, flexible material, such as thin, narrow strips of polymer films or sheets, can be used for the strands of material 308. Additionally, narrow fabrics, such as webbings made from woven materials can also be used. Further, the strands of material 308 can be composed of synthetic or natural fibers, yarns, or fine rope, for example. In one preferred embodiment, the strands of material 308 are configured to have considerable friction against human skin to further increase holding power.

As shown in FIGS. 5-6, the flexible strands of material 308 are woven at a helix angle to achieve the tubular shape of the sleeve accessory 300. The helix angle is used to generate constrictive forces upon axial application of tension forces. A variety of braid constructions of the strands of material 308 could be used to achieve this conversion of axial tension to circumferential constriction. In an embodiment, the strands of material 308 are woven to form a braided construction or pattern having approximately ½ inch spacing between each strand of material 308 at a helix angle of approximately 45 degrees with respect to the longitudinal y-y axis of the tubular shape (sleeve accessory 300). Other spacing of the strands of material 308 and helix angles could be used, as should be understood by a person of ordinary skill in the art in conjunction with a review of this disclosure. With greater spacing, the strands of material 308 will impinge into tissue to a greater degree than lower spacing. Additionally, lower spacing between strands of material 308 will more evenly distribute forces.

Further, lower helix angles will decrease circumferential constriction around the leg. However, excessively high helix angles will allow too much expansion axially, causing excessive travel and insufficient circumferential constriction. In one preferred embodiment, the spacing between the strands of material 308 is within the range of ¹⁄₁₆ inch to 1 inch, center to center. Additionally, in one preferred embodiment, the helix angles range from 20 degrees from the longitudinal y-y axis of the strands of material 308 to 70 degrees from the longitudinal y-y axis of the strands of material 308 are recommended.

While not necessary, it is beneficial to have the strands of material 308 take a conical shape at rest to better conform to the leg shape as its diameter transitions from thigh to knee to calf to just above the ankle (i.e., from the proximal end 302 of the sleeve accessory 300 to the distal end 304 of the sleeve accessory 300). As described above, the strands of material 308 are woven into a braided construction. In one preferred embodiment, the braided construction is, as with most finger traps, created by weaving a first strand over and a second strand under. However, other braided constructions or patterns with a different number of fibers (i.e., strands of material 308) crossed on each path over and under can be used.

As shown in FIG. 5, the sleeve accessory 300 is composed of strands of material 308 having a diameter and length suitable for placement over a patient's leg. The size and shape of the sleeve accessory 300 can be customized to fit legs of varying sizes and shapes. As shown in FIG. 5, the proximal end 302 of the sleeve accessory 300 comprises proximal ends 310 of the strands of material 308. The proximal end 310 of each strand of material 308 is finished such that each strand of material 308 is woven to return back into itself, creating looped proximal ends 310. In alternative embodiments, the proximal ends 310 are finished with an elastic fiber cuff, a non-elastic fiber cuff, or any other means suitable for retaining the proximal ends 310 of the strands of material 308 to prevent fraying or unraveling of the braid construction.

As shown in FIG. 5, the sleeve accessory 300 is used in conjunction with a surgical boot 10. In the depicted embodiment, the surgical boot 10 is L-shaped, comprising a proximal portion 18 for the leg of the patient and a distal portion 20 for the foot of the patient. The proximal portion 18 is configured to cradle the calf of the patient and retain the leg in the surgical boot 10, preventing medial or lateral movement of the calf. The distal portion 20 restrains the foot, roughly in the region of the metatarsal heads, to prevent medial or lateral motion of the foot. The retaining action also allows the patient to be placed into internal or external foot rotation. The surgical boot provides positioning control and rotational control of the patient's foot and leg, as needed. For example, the surgical boot 10 allows for knee flexion and extension while not under traction and allows for internal and external foot rotation while under traction and not under traction.

As shown in FIG. 6, the surgical boot 10 comprises a heel cutout 21 where the proximal portion 18 meets the distal portion 20. The heel cutout 21 provides an area to relieve the posterior of the patient's heel, preventing contract pressure wounds while the patient is unconscious during the procedure. The sleeve accessory 300 may also be used in a similar fashion with the surgical boot 10 shown in FIGS. 1-4 and described above.

Referring back to FIG. 5, the distal end 304 of the sleeve accessory 300 comprises distal ends 312 of the strands of material 308. The distal ends 312 of the strands of material 308 are left unbraided. In the embodiment shown in FIG. 6, the distal ends 312 of the strands of material 308 are unbraided from the ankle 104 of the patient. As shown in FIG. 5, the distal ends 312 of the strands of material 308 are gathered around the distal portion 20 of the surgical boot 10 at a collection point 314 so that tension may be applied thereto.

As shown in FIGS. 5 and 6, the collection point 314 is at an eyelet 316 on a distal connector 318. The eyelet 316 is used to gather all the distal ends 312 of the strands of material 308 at the collection point 314 so that tension may be applied to strands of material 308 to induce circumferential compression, allowing the leg 100 to be put into tension at the patient's hip. In the depicted embodiment, the distal connector 318 is a screw; however, any other known connector may be used. As shown, the distal connector 318 is used to attach the sleeve accessory 300 to a tension frame 320. In the embodiment in FIGS. 5 and 6, the tension frame 320 is U-shaped, such that a proximal side 322 of the tension frame 320 is substantially flush against the surgical boot 10 and the distal side 324 of the tension frame 320 has the distal connector 318 attached thereto.

As shown in FIGS. 5 and 6, wherein the distal connector 318 is a screw, the screw 318 extends through the distal side 324 of the tension frame 320. The screw 318 extends through the distal side 324 of the tension frame 320 and it is locked in place by a nut 326 or another known locking means. In the depicted embodiment, the nut 326 includes one or more cranks 328 attached thereto. Rotating the crank(s) 328 rotates the nut 326 to tension the distal ends 312 of the strands of material 308 by advancing the eyelet 316 in the screw 318 in the distal direction. In alternative embodiments, other tensioning mechanisms can be used, such as a pulley system, a winch system, and a rack and pinion system, for example.

As shown in FIGS. 5 and 6, a ball joint 330 is connected to and extends from the U-shaped tension frame 320 between the proximal and distal sides 322, 324. The ball joint 330 is sized and configured for attachment to a distractor apparatus (not shown). In use, a patient is positioned on an operating table 400 such that his or her leg 100 extends over an edge 402 of the table 400, as shown in FIG. 6. The foot 102 and leg 100 of the patient is extended through the inner volume 306 of the sleeve accessory 300 such that the proximal end 302 of the sleeve accessory 300 is around the leg 100 of the patient and the distal ends 312 of the strands of material 308 of the sleeve accessory 300 extend around the ankle 104 of the patient.

Thereafter, the leg 100 and foot 102 of the patient is positioned in the surgical boot 10 such that the foot 102 is in the distal portion 20 and the leg (calf) 100 of the patient is in the proximal portion 18, with the heel 106 of the patient extending through the heel cutout 21. The distal portion 20 of the surgical boot 10 is positioned against the proximal side 322 of the tension frame 320. As shown in FIG. 6, the distal ends 312 of the strands of material 308 of the sleeve accessory 300 are pulled around the distal portion 20 of the surgical boot 10 and gathered and attached to the eyelet 316 of the screw 318. The cranks 328 are rotated to tighten the screw 318 and tension the sleeve accessory 300. With the sleeve accessory 300 tensioned, the ball joint 330 is inserted into the hip distractor apparatus (not shown). The distractor apparatus can then be used to provide knee flexion/extension, hip flexion/extension, and internal/external rotation of the foot 102.

Figure 7:
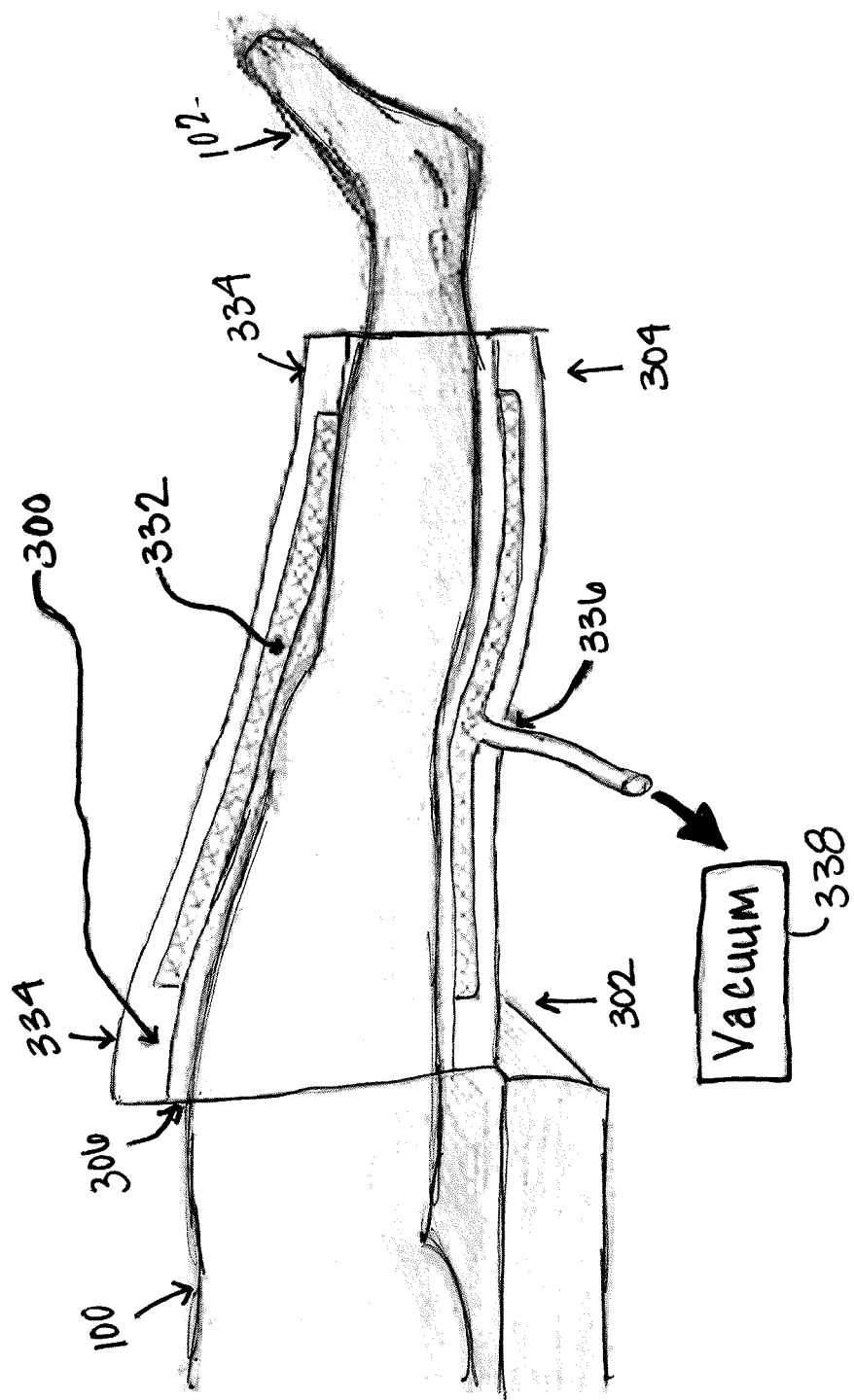
FIG. 7 is a cross-sectional side view schematic representation of a sleeve accessory in use, according to an alternative embodiment.
Figure 8:
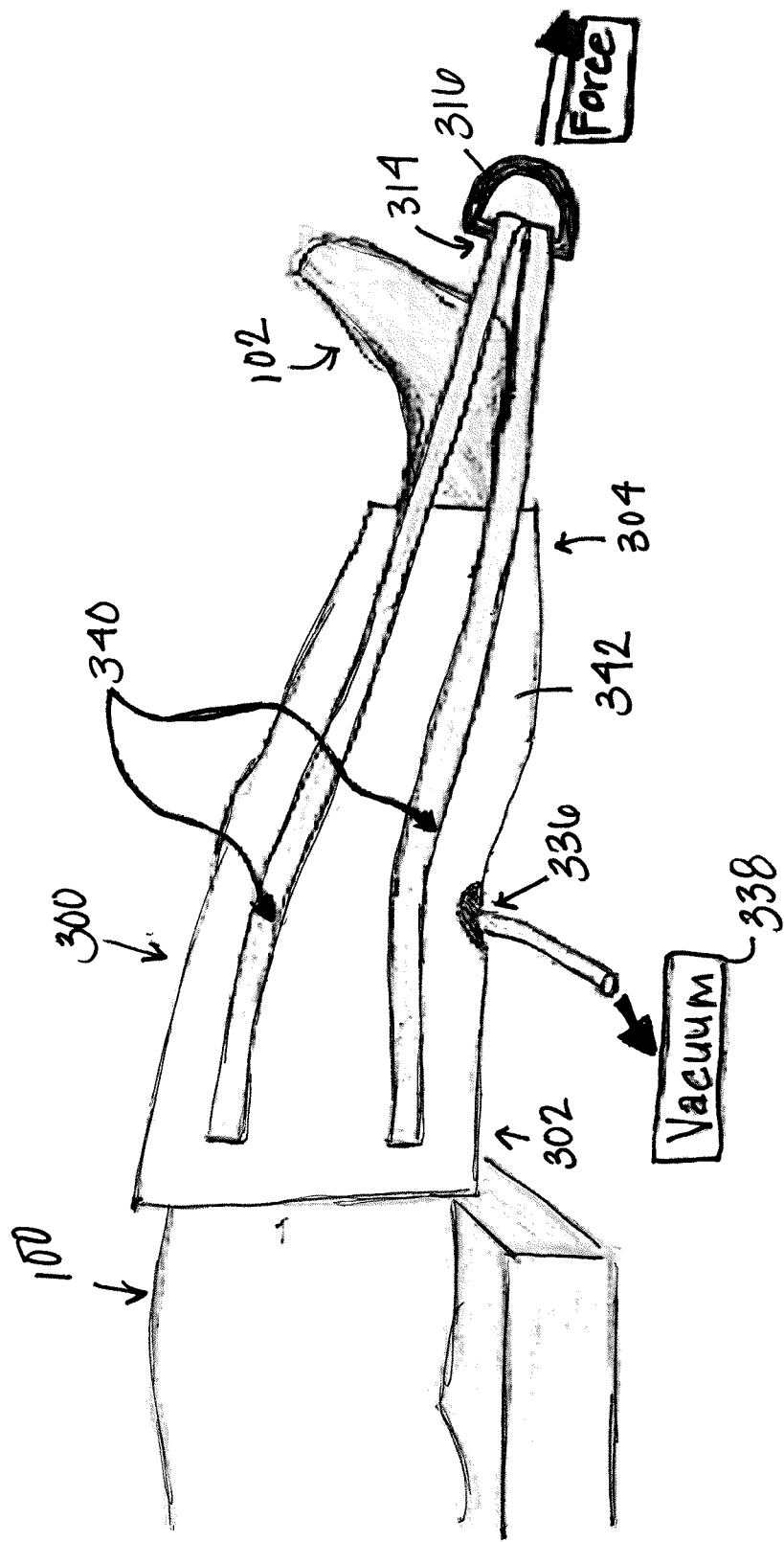
FIG. 8 is a side view schematic representation of a sleeve accessory in use, according to an alternative embodiment.

Referring now to FIGS. 7 and 8, there are shown side views schematic representations of a sleeve accessory 300, according to an alternative embodiment. The sleeve accessory shown in FIGS. 7 and 8 is a vacuum sleeve accessory 300. The vacuum sleeve accessory 300 is a tubular body, comprising an inner volume 306 sized and configured to accommodate the leg 100 of a patient. The sleeve accessory 300 is composed of a nonporous, elastomeric material, such as silicone or nitrile, for example. The sleeve accessory 300 is flexible to allow stretching to accommodate a wide range of shapes and sizes of legs 100. However, it is possible to construct the sleeve accessory 300 from stiffer, less flexible material if the size and shape of the sleeve accessory 300 is customized for a particular leg 100 shape and size.

As shown in FIG. 7, the sleeve accessory 300 comprises an internal material 332. In the depicted embodiment, the internal material 332 extends along at least a portion of the sleeve accessory 300. For example, the internal material extends along the entire sleeve accessory 300 up to 1 inch from the proximal end 302 and 1 inch from the distal end 304. The proximal end 302 and distal end 304 of the sleeve accessory 300 thus serve as seal regions 334. As air cannot escape the proximal end 302 and distal end 304 without the internal material 332, the seal regions 334 may seal in an airtight fashion directly against the skin of the patient's leg 100. The seal regions 334 serve to seal or close the sleeve accessory 300, allowing for a vacuum to be achieved and maintained inside the sleeve accessory 300.

Further, as shown in FIG. 7, the internal material 332 lines the sleeve accessory 300 around the inner volume 306. The internal material 332 can be stretchable, preferably porous, material with "air wicking" properties that allows air from the inner volume 306 of the sleeve accessory 300 to escape to the environment outside the sleeve accessory 300. A vacuum port 336 extends from the internal material 332 to the environment outside the sleeve accessory 300, as shown in FIG. 7. The vacuum port 336 has a connector (not shown) suitable for interfacing with a vacuum source 338.

As shown in FIG. 8, the sleeve accessory 300 can additionally include one or more external straps 340. The external straps 340 are composed of non-stretch material or fabric. The external straps 340 are fixed to an exterior 342 of the sleeve accessory 300. The external straps 340 extend from the proximal end 302 of the sleeve accessory 300 toward the distal end 304. As shown in FIG. 8, the external straps 340 extend past the distal end 304 of the sleeve accessory 300 and distal the foot 102 of the patient to a collection point 314.

In the embodiment shown in FIG. 8, the collection point 314 is at a ring 316. The external straps 340 are attached to the ring 316. The ring 316 acts a single point from which tension forces are applied, resulting in distraction of the hip joint while the friction of the internal (air wicking) material 332 compressed against the skin by vacuum forces provide holding power, keeping the leg positively held by the sleeve accessory 300 while the tension forces necessary for hip distraction are generated, held, and released. The sleeve accessory 300 is an improvement over traditional methods for hip distraction because the sleeve accessory 300 does not grab the knee or ankle of the patient. Therefore, the tension forces are only applied at the hip.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A surgical sleeve assembly, comprising:
   an L-shaped rigid shell having an inner volume, a proximal portion, and a distal portion having an outer distal surface;
   a tubular body having a proximal end and a distal end with an inner volume extending therebetween with a central longitudinal axis extending therethrough;
   wherein the tubular body is comprised of one or more strands of material woven into a braided construction and a portion of the tubular body extends within the inner volume of the L-shaped rigid shell;
   a helix angle measured between the central longitudinal axis and one of the one or more strand of material; and
   a collection point distal relative to the distal end of the tubular body wherein a distal end of each of the one or more strands of material is gathered, the collection point being positioned distal to the distal surface of the L-shaped rigid shell.

2. The assembly of claim 1, further comprising a U-shaped tension frame having a proximal side and a distal side, wherein the collection point is at a connector extending through the distal side of the tension frame.

3. The assembly of claim 2, wherein the connector tensions the one or more strands of material.

4. The assembly of claim 2, further comprising a ball joint extending from the tension frame between the proximal side and the distal side.

5. The assembly of claim 2, wherein the distal portion of the L-shaped rigid shell is against the proximal side of the tension frame.

6. The assembly of claim 5, wherein the distal end of each of the one or more strands of material extends around the distal portion of the L-shaped rigid shell to the collection point.

7. The assembly of claim 1, wherein the helix angle is within the range of 20° to 70°.

8. The assembly of claim 1, wherein the helix angle is 45°.

* * * * *